US012465378B2

United States Patent

(12) United States Patent
McAteer et al.
(10) Patent No.: US 12,465,378 B2
(45) Date of Patent: Nov. 11, 2025

(54) PLATELET-RICH PLASMA ACTIVATION SYSTEM AND METHOD

(71) Applicant: Curative Sound, LLC, Carmel, IN (US)

(72) Inventors: Jeffrey Phillip McAteer, Carmel, IN (US); James V. Olson, Jr., Indianapolis, IN (US); Randal Douglas Wood, New Palestine, IN (US); Geoffry N. Barber, New Castle, IN (US)

(73) Assignee: Curative Sound, LLC, Carmel, IN (US)

( * ) Notice: Subject to any disclaimer, the term of this patent is extended or adjusted under 35 U.S.C. 154(b) by 539 days.

(21) Appl. No.: 18/061,290

(22) Filed: Dec. 2, 2022

(65) Prior Publication Data

US 2023/0172623 A1 Jun. 8, 2023

Related U.S. Application Data

(60) Provisional application No. 63/264,904, filed on Dec. 3, 2021.

(51) Int. Cl.
*A61B 17/22* (2006.01)
*A61N 7/00* (2006.01)

(52) U.S. Cl.
CPC ...... *A61B 17/22* (2013.01); *A61N 2007/0078* (2013.01)

(58) Field of Classification Search
CPC ........... A61B 17/22; A61N 2007/0078; A61M 2202/0427; A61M 1/0281; A61K 35/16; C12N 5/0644; C12N 2529/00
See application file for complete search history.

(56) References Cited

U.S. PATENT DOCUMENTS 4,526,168 A 7/1985 Hassler et al.
6,431,476 B1 8/2002 Taylor et al.
(Continued)

FOREIGN PATENT DOCUMENTS

KR 1020150113978 10/2015

OTHER PUBLICATIONS

Wu, Yue, Murugappan Suresh Kanna, Chenhui Liu, Yufeng Zhou "Generation of Autologous Platelet-Rich Plasma by the Ultrasonic Standing Waves". IEEE Transaction on Biomedical Engineering, vol. 63, No. 8, Aug. 2016. (Year: 2016).*
(Continued)

*Primary Examiner* — Michael L Hobbs
(74) *Attorney, Agent, or Firm* — Maginot, Moore & Beck

(57) ABSTRACT

A platelet-rich plasma (PRP) activation system for activating PRP contained in a container includes a housing, a power supply, a piezoelectric transducer array, a support structure, and a coupling medium. The power supply is located in the housing. The piezoelectric transducer array is operably connected to the power supply and is located in the housing. The piezoelectric transducer array is configured to generate a focused shock wave using power from the power supply. The support structure is operably connected to the housing and is configured (i) to receive the container, and (ii) to position the container at least partially within the housing, such that at least a portion of the PRP is located at a focal volume formed by the focused shock wave. The coupling medium is located in the housing and is positioned between the piezoelectric transducer array and the container.

20 Claims, 10 Drawing Sheets

(56) References Cited

U.S. PATENT DOCUMENTS

| | | | |
|---|---|---|---|
| 6,780,161 | B2 | 8/2004 | Faragalla et al. |
| 9,555,267 | B2 | 1/2017 | Ein-Gal |
| 2021/0113621 | A1 | 4/2021 | Centeno et al. |

OTHER PUBLICATIONS

Notarnicola, A. et al., "Effect of shock wave treatment on platelet-rich plasma added to osteoblast cultures", Ultrasound in Med. & Biol., 2011, vol. 37. No. I, pp. 160-168.

International Search Report corresponding to PCT Application No. PCT/EP2022/080842, mailed Apr. 25, 2023 (English language document) (16 pages).

Renz, et al., Effects of Shock Waves on Chondrocytes and Their Relevance in Clinical Practice, May 2009 (2 pages).

Frairia, et al., High Energy Shock Waves (HESW) Enhance Paclitaxel Cytotoxicity in MCF-7 Cells, Oct. 2003 (10 pages).

Dietz-Laursonn, et al., In-vitro Cell Treatement with Focused Shockwaves, Journal of Therapeutic Ultrasound, 2016 (14 pages).

Seabaugh, et al., Extracorporeal Shockwave Therapy Increases Growth Factor Release from Equine Platelet-Rich Plasma In Vitro, frontiers in Veterinary Science, Dec. 7, 2017 (6 pages).

* cited by examiner

PLATELET-RICH PLASMA ACTIVATION SYSTEM AND METHOD

This application claims the benefit of priority of U.S. provisional application Ser. No. 63/264,904, filed on Dec. 3, 2021 the disclosure of which is herein incorporated by reference in its entirety.

FIELD

This disclosure relates to the field of platelet-rich plasma (PRP) therapy and, in particular, to activating the PRP before administration to a patient.

BACKGROUND

PRP therapy is a process in which PRP, also known as autologous conditioned plasma, is injected into a patient (human or animal) at an injury site to stimulate the healing process. PRP is a concentrate of platelet-rich plasma protein derived from whole blood that has been centrifuged to remove red blood cells and platelet-poor plasma. Typical injuries in which PRP therapy is utilized include injured tendons, ligaments, muscles, and joints. PRP therapy is also effective for treating osteoarthritis. Moreover, PRP therapy is used as a treatment option following oral surgery and plastic surgery. PRP therapy tends to reduce patients' need for anti-inflammatories and stronger medications like opioids. In addition, the side effects of PRP therapy are very limited because the PRP is typically extracted from the patient's blood. Allogeneic PRP therapy is also available for some treatments and injuries and also has very limited side effects.

During a PRP therapy session, the PRP is injected into the patient in an unactivated state or an activated state. Unactivated PRP includes growth factors useful for stimulating the healing process. Activating the PRP is a process in which the PRP is caused to release additional growth factors including vascular endothelial growth factor (VEGF), transforming growth factor-beta (TGF-β), and platelet-derived growth factor (PDGF). The additional quantity of growth factors released by the activated PRP tends to further stimulate the healing process.

There are several methods of activating PRP for PRP therapy. One method includes subjecting the PRP to a freeze-thaw cycle, which requires refrigeration equipment and, typically, multiple days between drawing the patient's blood and providing the patient with the PRP injection. Another method of activating PRP includes mixing the PRP with calcium chloride ($CaCl_2$) and/or thrombin. This method of activation, however, is known to undesirably cause clotting of the PRP, which increases the difficulty in administering the activated PRP to the patient and may reduce the effectiveness of the PRP therapy. Thus, known methods for activating PRP are either time-consuming, increase the difficulty in administering the treatment, and/or reduce the effectiveness of the treatment.

Based on the above, further advancements are needed to improve the process for activating the PRP used in PRP therapy.

SUMMARY

According to an exemplary embodiment of the disclosure, a platelet-rich plasma (PRP) activation system for activating PRP contained in a container includes a housing, a power supply, a piezoelectric transducer array, a support structure, and a coupling medium. The power supply is located in the housing. The piezoelectric transducer array is operably connected to the power supply and is located in the housing. The piezoelectric transducer array is configured to generate a focused shock wave using power from the power supply. The support structure is operably connected to the housing and is configured (i) to receive the container, and (ii) to position the container at least partially within the housing, such that at least a portion of the PRP is located at a focal volume formed by the focused shock wave. The coupling medium is located in the housing and is positioned between the piezoelectric transducer array and the container. The coupling medium is configured to transmit the focused shock wave from the piezoelectric transducer array to the container.

According to another exemplary embodiment of the disclosure, a platelet-rich plasma (PRP) activation system for activating PRP contained in a container includes a housing, a power supply, a first piezoelectric transducer array, a second piezoelectric transducer array, and a support structure. The power supply is located in the housing. The first piezoelectric transducer array is operably connected to the power supply and is located in the housing. The first piezoelectric transducer array is configured to generate a first focused shock wave using power from the power supply. The second piezoelectric transducer array is operably connected to the power supply and is located in the housing. The second piezoelectric transducer array is configured to generate a second focused shock wave using the power from the power supply. The support structure is operably connected to the housing and is configured (i) to receive the container, and (ii) to position the container at least partially within the housing along a movement axis of the container, such that a first portion of the PRP is located at a first focal volume formed by the first focused shock wave and a second portion of the PRP is located at a second focal volume formed by the second focused shock wave. The first focal volume and the second focal volume are spaced apart from each other along the movement axis.

According to a further exemplary embodiment of the disclosure, a method of operating a platelet-rich plasma (PRP) activation system includes striking a first portion of PRP with a first focused shock wave generated by a first piezoelectric transducer array of the PRP activation system in order to activate the first portion of the PRP. The PRP is contained in a container received by the PRP activation system, and the container is located at a first position. The method further includes moving the container along a movement axis from the first position to a second position with a positioning device of the PRP activation system, and striking a second portion of the PRP with a second focused shock wave generated by the first piezoelectric transducer array in order to activate the second portion of the PRP. The container located at the second position.

BRIEF DESCRIPTION OF THE FIGURES

The above-described features and advantages, as well as others, should become more readily apparent to those of ordinary skill in the art by reference to the following detailed description and the accompanying figures in which.

DETAILED DESCRIPTION

Figure 1:
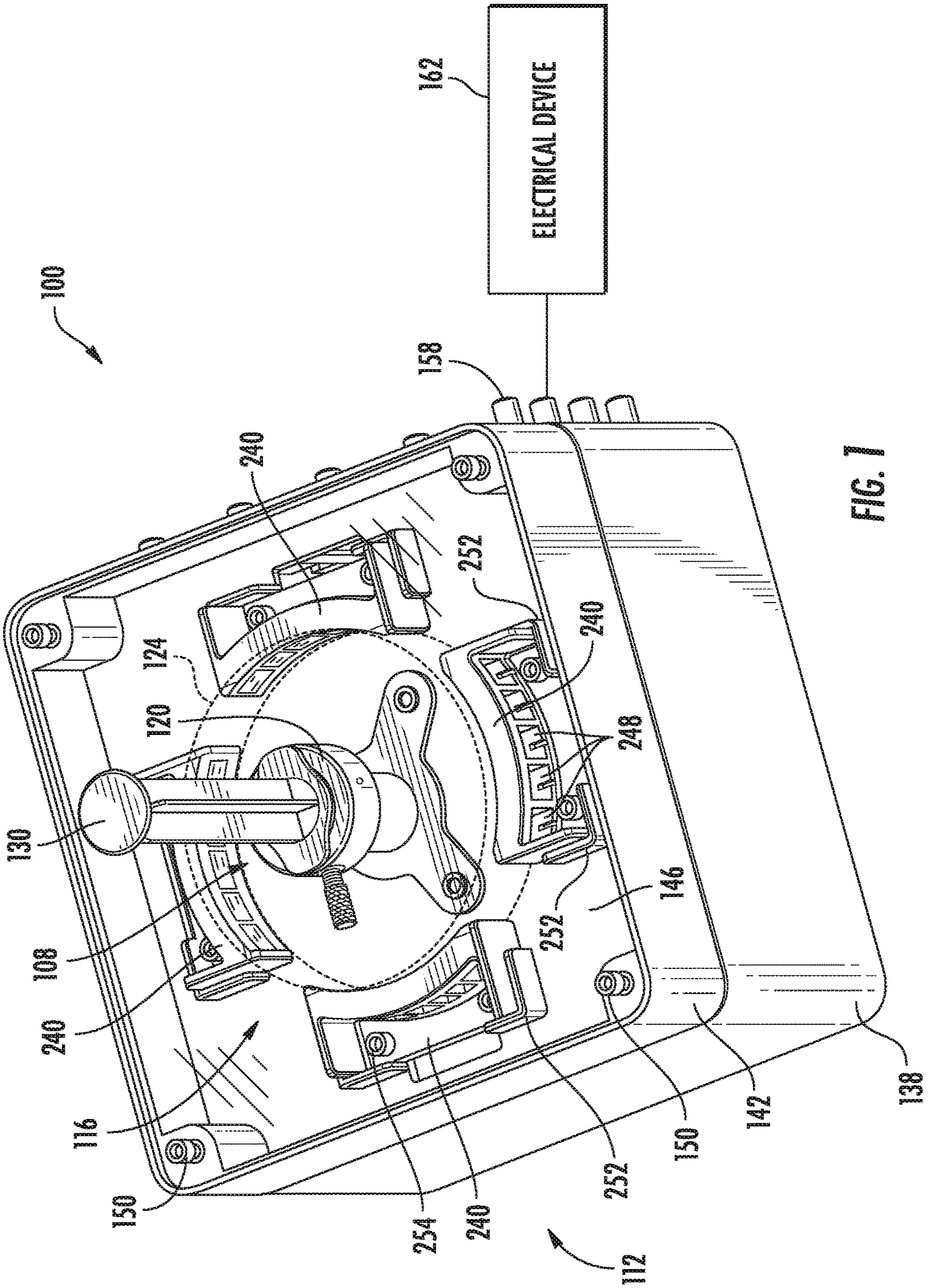
FIG. 1 illustrates a PRP activation system, as disclosed herein, including a container inserted into the PRP activation system.

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

Aspects of the disclosure are disclosed in the accompanying description. Alternate embodiments of the disclosure and their equivalents may be devised without parting from the spirit or scope of the disclosure. It should be noted that any discussion herein regarding “one embodiment”, “an embodiment”, “an exemplary embodiment”, and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

For the purposes of the disclosure, the phrase “A and/or B” means (A), (B), or (A and B). For the purposes of the disclosure, the phrase “A, B, and/or C” means (A), (B), (C), (A and B), (A and C), (B and C), or (A, B and C).

The terms “comprising,” “including,” “having,” and the like, as used with respect to embodiments of the disclosure, are synonymous.

Figure 2:
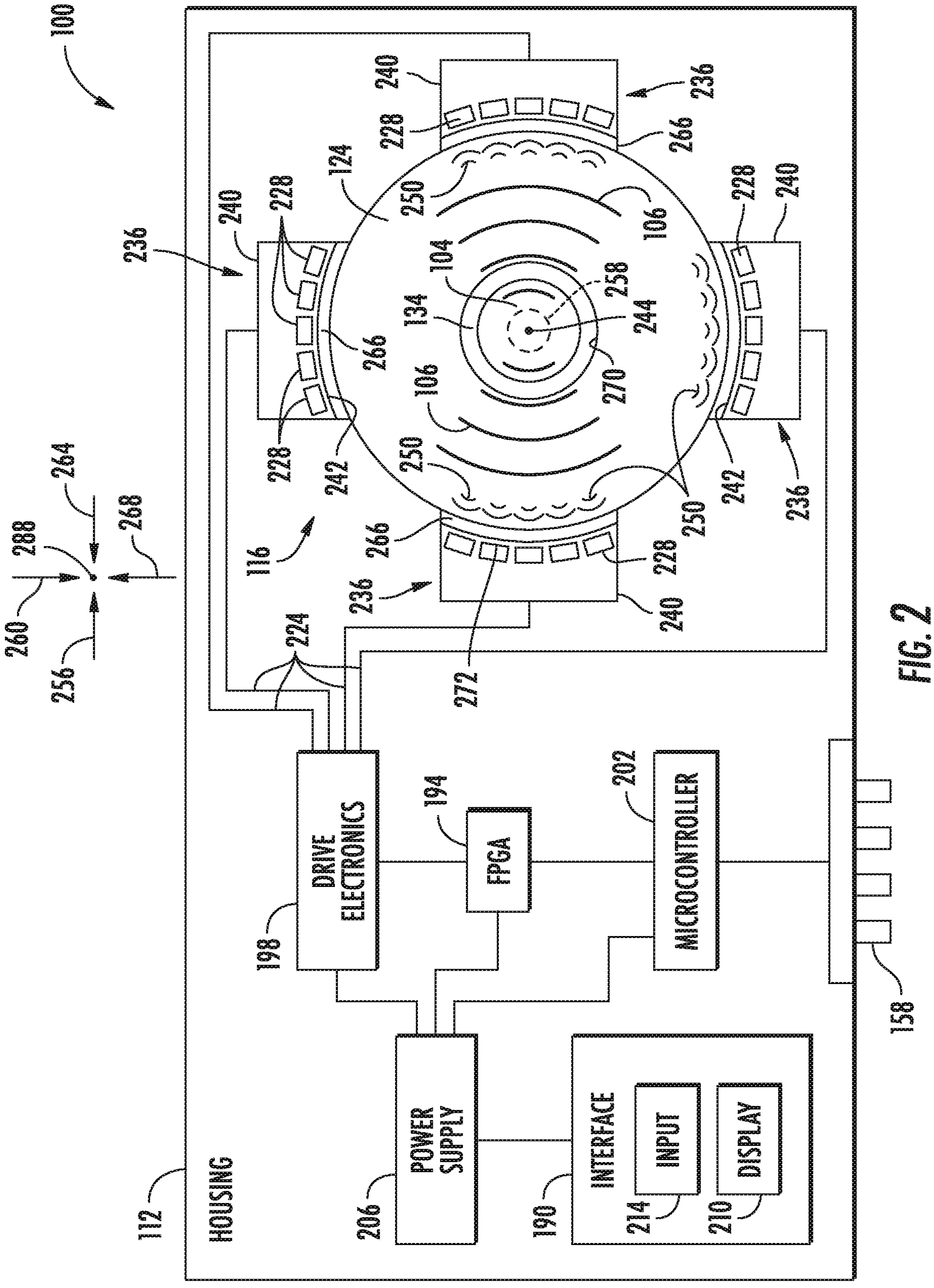
FIG. 2 is a block diagram of the PRP activation system of FIG. 1.

As shown in FIGS. 1 and 2, a PRP activation system 100 is configured to activate PRP 104 (FIG. 2) before a clinician injects the PRP 104 into a patient in the course of PRP therapy. The PRP activation system 100 uses focused acoustical shock waves 106 to activate the PRP 104 instead of the freeze-thaw cycle and instead of adding calcium chloride and/or thrombin to the PRP 104. Activating the PRP 104 with the activation system 100 takes less than three minutes. Accordingly, the PRP activation system 100 overcomes the equipment difficulties (no refrigeration equipment is needed) and the time requirements of the freeze-thaw cycle activation approach. Moreover, shock waves, such as the focused shock waves 106, have been found to result in a significant increase in growth factors in the PRP 104 without the clotting issues of calcium chloride and/or thrombin. As explained herein, the PRP activation system 100 is a portable and efficient system for activating PRP 104, thereby increasing patient comfort and convenience, and decreasing the time required to prepare the PRP 104 for injection during PRP therapy.

With reference to FIG. 1, the PRP activation system 100 is configured to receive a container 108 of PRP 104 (FIG. 2). In the figures, the container 108 is shown as a syringe, but the container 108 may additionally or alternatively be provided as a vial or any other suitable vessel. The PRP activation system 100 includes a housing 112, a shock wave generator assembly 116, a container support structure 120, and a coupling medium 124. The exemplary container 108 includes a plunger 130 and a barrel 134 (FIG. 2). In one embodiment, the housing 112 includes a base structure 138, an intermediate structure 142 connected to the base structure 138, and a cover or lid 146 connected to the intermediate structure 142 with fasteners 150. The base structure 138 and the intermediate structure 142 define a housing space 154 (FIG. 3) configured to receive operating electronics of the PRP activation system 100. The intermediate structure 142 is configured to support the shock wave generator assembly 116 and the coupling medium 124. The lid 146 is configured to close, at least partially, the housing space 154. In an exemplary embodiment, the lid 146 is formed from a translucent material, such as acrylic. In other embodiments, the lid 146 is transparent or opaque and is formed from another suitable material. Moreover, in a further embodiment, the base structure 138 and the intermediate structure 142 are integrally formed as a single piece.

In some embodiments, as shown in FIG. 1, the base structure 138 also supports a plurality of electrical connectors 158, such as the illustrated subminiature version a (SMA) connectors, for electrically connecting the PRP activation system 100 to an external electrical device 162. In other embodiments, the electrical connectors 158 are provided as any other suitable electrical connector format, such as a serial port and/or a universal serial bus (USB). In further embodiments, such as the PRP activation system 700 of FIG. 10, the PRP activation system 100 does not include the electrical connectors 158 and an interface 190, 708 is used to control the system 100.

As shown in the block diagram of FIG. 2, the operating electronics of the PRP activation system 100 include an interface 190, a field programmable gate array (FPGA) 194, and drive electronics 198, each operably connected to a microcontroller 202. The PRP activation system 100 also includes a power supply 206 within the housing 112. Each of these elements is described herein.

The interface 190, which is not shown in FIG. 1, includes a display 210 and an input device 214 configured for operation by a user of the PRP activation system 100. The display 210 is mounted on the housing 112 and is configured to display information and data pertaining to operation of the PRP activation system 100, such as a number of the focused shock waves 106 to be administered to the PRP 104, an energy level of the focused shock waves 106, and a repetition frequency of the focused shock waves 106. In one embodiment, the display 210 is a liquid crystal display (LCD).

The input device 214 is mounted on the housing 112 and is configured to generate input data when touched or pressed by the operator. For example, the input device 112 may be pressed to generate an electrical start signal for initiating a shock wave sequence for activating the PRP 104 within the container 108. An exemplary input device 214 includes at least one push button.

In one embodiment, the input device 214 and the display 210 are combined as a touchscreen mounted on the housing 112. In a further embodiment, the PRP activation system 100 does not include the interface 190, and the operator interfaces with the PRP activation system 100 through the external electrical device 162 connected to electrical connectors 158. The external electrical device 162 is configured as a laptop computer, a desktop computer, a signal generator, a tablet computer, a smartphone, and/or any other suitable computer device. In some embodiments, the external device 162 is wirelessly connected to the PRP activation system 100 via Bluetooth® or any other suitable wireless connection and data transfer protocol.

As shown in FIG. 2, the FPGA 194 is configured to receive an activation signal from the microcontroller 202, such as when the user operates the input device 214, and causes the start signal for initiating the focused shock waves 106 to be generated. The activation signal causes the FPGA 194 to activate the drive electronics 198 for generating high-power electric signals that are supplied to the shock wave generator assembly 116 for generating the focused shock waves 106.

The drive electronics 198 of FIG. 2 are operably connected to the shock wave generator assembly 116 and are configured to generate high-voltage and high-current signals that are supplied to the shock wave generator assembly 116 through transducer channels 224 for causing the shock wave generator assembly 116 to generate the focused shock waves 106. In one embodiment, the drive electronics 198 include a separate drive channel electronic unit (not shown) for each shock wave generating element 228 of the shock wave generator assembly 116. Accordingly, the drive electronics 198 may include twenty drive channel electronic units for the twenty shock wave generating elements 228.

The microcontroller 202 is provided as any desired processor, microprocessor, controller, and/or microcontroller. In a specific embodiment, the microcontroller 202 is a 32F413 microprocessor by STMicroelectronics.

The power supply 206, in the exemplary embodiment of FIG. 2, is a power source for generating the focused shock waves 106 and for powering all electronics of the PRP activation system 100. In one embodiment, the power supply 206 includes at least one rechargeable battery located within the housing 112. For example, the power supply 206 includes a rechargeable lithium-ion battery or any other suitable battery technology having a high power density. In such an embodiment, no connection to a wall outlet supply of electricity (i.e., mains power) is required to generate the focused shock waves 106. That is, in some embodiments, the power supply 206, as a rechargeable battery, is the only power source for generating the focused shock waves 106. As such, the PRP activation system 100 is portable and can be operated anywhere. In another embodiment, the power supply 206 is a switching power supply and/or a linear power supply configured for connection to the wall outlet supply of electricity. The power supply 206 is located in the housing 112.

As shown in FIG. 2, the shock wave generator assembly 116 includes four concentrically-arranged transducer arrays 236, each operably connected to the power supply 206. Each transducer array 236 is configured to generate a corresponding focused shock wave 106 using power from the power supply 206. Each transducer array 236 is located in the housing 112 and includes a corresponding support frame 240 and five of the shock wave generating elements 228. The support frames 240 are each mounted to the intermediate structure 142 (FIG. 1) and are positioned around the coupling medium 124. The support frames 240 define an arc-shaped surface 242 facing the coupling medium 124. The coupling medium 124 and the transducer arrays 236 are concentrically arranged about a center point 244. When the container 108 is supported by the support structure 120, the center point. 244 is located within a volume of the container 108 that contains the PRP 104. In other embodiments, the shock wave generator assembly 116 includes from one to forty of the transducer arrays 236.

With reference again to FIG. 1, each support frame 240 defines a plurality of cavities 248 for receiving a corresponding one of the shock wave generating elements 228. In the illustrated example, each support frame 240 defines five of the cavities 248. The cavities 248 extend completely through the support frames 240 and form openings in the arc-shaped surface 242. The cavities 248 extend from the arc-shaped surface 242 into the support frame 240. In other embodiments, each support frame 240 may define from one to twenty of the cavities 248 at least some of which are configured to receive a corresponding shock wave generating element 228.

The support frames 240, as shown in FIG. 1, are formed from a rigid thermoplastic or another suitably rigid and generally non-electrically conductive material. Moreover, in one embodiment, each support frame 240 is positioned within a corresponding positioning jig 252 (FIG. 1) of the intermediate structure 142 and is attached to the intermediate structure 142 by fasteners 254. The positioning jigs 252 "aim" the transducer arrays 236 (FIG. 2) so that the resulting focused shock waves 106 are aimed and/or focused at the center point 244 and form a focal volume 258 within the container 108. The positioning jigs 252 also simplify assembly of the PRP activation system 100.

As shown in FIG. 2, the shock wave generating elements 228 of the transducer arrays 236 are configured to generate individual acoustical shock waves 250 for activating the PRP 104 within the container 108. The individual shock waves 250 generated by the elements 228 are sound waves. In particular, the individual shock waves 250 are short duration, acoustic pulses having a very high positive pressure amplitude and a steep pressure increase compared to the ambient pressure. Shock waves are similar to ultrasound but have a different wave profile. Typically, ultrasound waves have a periodic oscillation between positive and negative pressure along with a narrow bandwidth. Whereas, shock waves typically exhibit a single positive pressure pulse containing a broad bandwidth. Shock waves are different than radial pressure pulses due to their higher pressure, faster rise time, shorter duration, and ability to be focused. Radial pressure waves are not shock waves and cannot be focused.

In an exemplary embodiment, the shock wave generating elements 228 are piezoelectric elements and the transducer arrays 236 are configured as piezoelectric transducer arrays 236. The piezoelectric elements are each configured to generate the individual shock waves 250 in response to receiving the high voltage and high current signal from the drive electronics 198. In a specific embodiment, the shock wave generating elements 228 are “dice-and-fill” composite piezoelectric material and epoxy having vertical columns of piezoceramic material. These elements 228 have higher efficiency (coupling coefficients) and a lower acoustic impedance that is easier to match to water or tissue. Additionally, the shock wave generating elements 228 are constructed using a “soft” piezoceramic material having a high dielectric constant and high coupling. In other embodiments, the shock wave generating elements 228 are formed from any other suitable material or materials.

The shock wave generating elements 228 are arranged at least partially in the cavities 248 in the support frames 240 along the arc-shaped surface 242. Each individual shock wave 250 is emitted from a corresponding face 272 (FIG. 2) of one of the shock wave generating elements 228. Accordingly, due to the shape of the arc-shaped surface 242 the individual shock waves 250 converge, constructively combine, and/or are mechanically focused at the center point 224, at the focal volume 258, and/or at another predetermined point within the container 108 as the focused shock waves 106. Each transducer array 236 of the PRP activation system 100 is configured to generate a corresponding one of the focused shock waves 106.

As shown in FIG. 2, the focal volume 258 is a three-dimensional space in which the focused shock waves 106 are delivered with an energy level that is suitable for activating the PRP 104. In one embodiment, the focal volume 258 is formed by a constructive combination of the focused shock waves 106. In the example of FIG. 2, the focal volume 258 is formed by the constructive combination of two of the focused shock waves 106, of three of the focused shock waves 106, or of four of the focused shock waves 106.

In order to further mechanically focus the individual shock waves 250, the microcontroller 202 configures the drive electronics 198 to activate each shock wave generating element 228 with a predetermined time delay and/or a predetermined time advance. The set of time delays and/or time advances for each of the elements 228 is referred to herein as a timing sequence and/or a timing program. When the shock wave generating elements 228 are activated according to the timing sequence, the individual shock waves 250 generated by the elements 228 arrive at the focal volume 258 simultaneously or substantially simultaneously as the focused shock wave 106. The timing sequence may cause each element 228 to be activated at a different time in order to form the focused shock wave 106. In an example, the timing sequence causes a first element 228 to be activated at a first time and causes a second element 228 to be activated at a second time that is different from the first time. The individual shock waves 250 generated by the two elements 228 arrive at the focal volume 258 substantially simultaneously. The first and second elements 228 may be located in the same transducer array 236 or in different transducer arrays 236.

As used herein, the focused shock wave 106 includes any constructive combination of two or more shock waves 250. Thus, as used herein, focusing refers to constructively combining shock waves 250 at the focal volume 258. The focused shock wave 106 can be formed by mechanical focusing in which the elements 228 are pointed at the same spot (i.e., the focal volume 258). The focused shock wave 106 can also be formed by using acoustic lenses and/or reflectors to focus the shock waves 250 at the focal volume 258. In some embodiments, the focused shock wave 106 is generated without using the time delays and/or time advances of the timing sequence. The timing sequence is not required to generate the focused shock wave 106. Focusing the shock waves 250 concentrates the pressure of the shock waves 250 at the focal volume 258.

In one embodiment, the predetermined time delays are based on a reference time delay. For example, the reference time delay is arbitrarily chosen as 500 ns. The time delays either lead, lag, or are equal to the reference time delay. The elements 228 generating individual shock waves 250 that lead the reference time delay, receive time delays less than the reference time delay, whereas the elements 228 generating individual shock waves 250 that lag the reference time delay receive time delays that are greater than the reference time delay. In an example, about 150 ns span between the first element 228 to be activated and the last element 228 to be activated during the generation of the focused shock wave 106.

The timing sequence(s) are stored in the FPGA 194, for example, or in a separate non-transitory electronic memory (not shown) of the PRP activation system 100. As used herein, “substantially simultaneously” means that the individual shock waves 250 each arrive at the focal volume 258 within plus or minus 20 nanoseconds to form a corresponding one of the focused shock waves 106.

As shown in FIG. 2, the shock wave generating elements 228 are arranged concentrically and are each approximately the same distance from the center point 244. Nevertheless, due to slight positioning and alignment differences (i.e., tolerances), when the shock wave generating elements 228 are each activated at the same time, at least some of the individual shock waves 250 arrive at the focal volume 258 at different times. The timing sequences account for the tolerances in the construction of the transducer arrays 236 and the structural differences in the shock wave generating elements 228, so that the individual shock waves 250 arrive at the focal volume 258 substantially simultaneously.

In one embodiment, the location of the focal volume 258 of the focused shock waves 250 is “tunable” (i.e., movable or positionable) to any location within the container 108 that is in a plane 262 (FIG. 3) of the shock wave generating elements 228. The location of the focal volume 258 is moved and/or tuned by changing and/or adjusting the timing delays applied to the shock wave generating elements 228 by the drive electronics 198. For example, with reference to FIG. 2, the focal volume 258 is moved closer to the left transducer array 236 by activating the elements 228 of the left transducer array 236 prior to activating the elements 228 of the right transducer array 236.

As shown in FIG. 2, the concentrically arranged transducer arrays 236 each emit the corresponding focused shock wave 106 toward the center point 244. Specifically, with reference to FIG. 2, the left transducer array 236 emits the focused shock wave 106 in a first direction 256 toward the center point 244, the top transducer array 236 emits the focused shock wave 106 in a different second direction 260 toward the center point 244, the right transducer array 236 emits the focused shock wave 106 in a different third direction 264 toward the center point 244, and the bottom transducer array 236 emits the focused shock wave 106 in a different fourth direction 268 toward the center point 244. The support structure 120 enables movement of the container 108 in directions along the movement axis 288 which are different from and perpendicular to the directions 256, 260, 264, 268.

The shock wave generator assembly 116, as illustrated in the figures, includes four of the transducer arrays 236 that each include five of the elements 228. The segmentation of the transducer array 236 into four separate segments provides benefits including providing a mechanical support for the cover 146. The segmented transducer array 236 also simplifies application of an impedance matching layer 266 (FIG. 2) to the elements 228. Moreover, having a segmented transducer array 236 enables repairs to the PRP activation system 100 by removing only the defective transducer array 236 instead of removing all of the transducer arrays 236 as is required with a unitary (non-segmented) transducer array 236 structure.

In other embodiments, the shock wave generator assembly 116 includes from one to twenty-four of the transducer arrays 236, and the transducer arrays 236 each include from one to ten of the elements 228. The transducer array 236 is referred to as an "array" even when it includes only one of the elements 228. In yet other embodiments, the shock wave generator assembly 116 includes a single transducer array 236 that extends from 90° to 360° around the center point 244.

The number of elements 228 included in the transducer array(s) 236 is based on a predetermined pressure level and/or predetermined energy level to be achieved at the focal volume 258 by the focused shock wave 106. Including more elements 228 in the generation of the focused shock wave 106 results in a greater pressure level at the focal volume 258, and including fewer elements 228 in the generation of the focused shock wave 106 results in less pressure at the focal volume 258.

For an element 228 having a shock wave generating area of 0.25 to 1.0 $cm^2$ it was found that twenty of the elements 228 generates a focused shock wave 106 at the focal volume 258 with a predetermined pressure level and/or predetermined energy level suitable for activating the PRP 104.

The shock wave generating elements 228 are positioned against an impedance matching layer 266 (FIG. 2) of the transducer arrays 236. In one embodiment, the matching layer 266 is applied to the arc-shaped surface 242 and the shock wave generating elements 228. The material(s) of the matching layer 266 is selected to transmit the individual shock waves 250 from the shock wave generating elements 228 to the coupling medium 124 with minimal reflection and with minimal attenuation. That is, the matching layer 266 steps the acoustical impedance down from the material(s) of the shock wave generating elements 228 to that of the coupling medium 124 to aid in energy transfer of the individual shock waves 250 and to avoid reflections of the individual shock waves 250 at the interface of the elements 228 and the coupling medium 124. The matching layer 266 includes composite epoxy and cerium oxide powder having specific mix ratios, in one embodiment. In other embodiments, the matching layer 266 is formed from any other suitable material. Moreover, in other embodiments, the transducer arrays 236 include multiple matching layers 266 of different materials.

Figure 3:
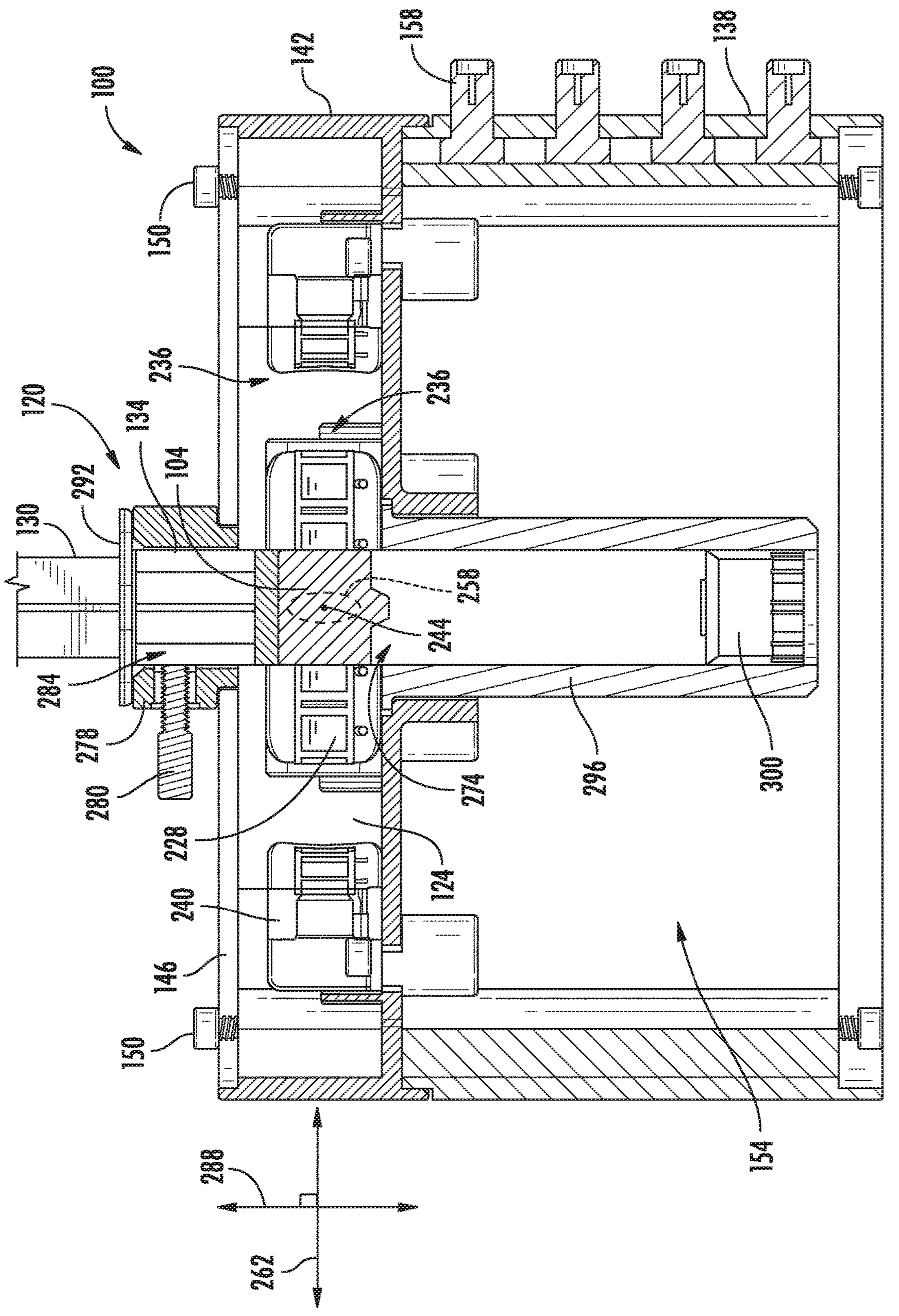
FIG. 3 is a cross sectional view of the PRP activation system of FIG. 1.

As shown in FIG. 2, the coupling medium 124 is located in the housing 112 between the transducer arrays 236 and the container 108 in the plane 262 (FIG. 3). Moreover, the coupling medium 124 is "sandwiched" between the lid 146 and the intermediate housing 142. Specifically, the coupling medium 124 extends from the matching layer 266 to the container 108. In one embodiment, the coupling medium 124 is positioned against and is in direct contact with the matching layer 226 and the container 108. The individual shock waves 250 generated by the transducer arrays 236 travel through the matching layer 266, through the coupling medium 124, and through the container 108 before arriving at the focal volume 258 inside of the container 108 as the focused shock waves 106.

In one embodiment, the coupling medium 124 is substantially cylindrical with a centrally located hole or opening 270 (FIG. 2) to receive the container 108. Thus, the coupling medium 124 is doughnut-shaped or shaped as a toroid. The material of the coupling medium 124 is selected to transmit the shock waves 106, 250 with minimal attenuation. In one embodiment, the coupling medium 124 is formed from hydrogel and/or another suitable hydrophilic polymer. Accordingly, the coupling medium 124 is disposable and is replaced periodically to achieve high levels of transmission of the shock waves 106, 250 to the PRP 104. In another embodiment, the coupling medium 124 is formed from a polymer-gel and tends not to require periodic replacement. For example, a more permanent coupling medium 124 is formed from styrene-ethylene-butylene-styrene (SEBS). It is noted that hydrogel tends to attenuate shock waves less than SEBS and results in a higher energy-flux density in the PRP 104 but, as mentioned, the coupling medium 124 formed from hydrogel typically requires periodic replacement.

As shown in FIG. 3, the support structure 120, which is also referred to herein as a container support, a collar support, and/or a mounting structure, includes a collar 278 and a set screw 280. The collar 278 is mounted on the lid 146 of the housing 112 and defines an opening 284 through which the container 108 extends. The support structure 120 receives the container 108 through the opening 284 so that the container 108 is positioned through the lid 146 and at least partially within the housing 112 (i.e., at least partially within the housing space 154). The set screw 280 is threadingly received by the collar 278 and is adjustable against the container 108 to hold the container 108 in a selected location along the movement axis 288. Accordingly, the container 108 is adjustable in position along the movement axis 288, relative to the transducer arrays 236, so that a predetermined portion of the PRP 104 can be positioned in the focal volume 258 to receive the focused shock waves 106. In one embodiment, a flange 292 of the container 108 prevents the container 108 from extending any further into the housing space 154 along the movement axis 288.

FIG. 3 also illustrates a support sleeve 296 and a base member 300 of the housing 112. The support sleeve 296 is received by the intermediate structure 142 and is configured to guide the container 108 into the PRP activation system 100. An opening 274 of the support sleeve 296 is centered at the center point 244. The base member 300 is an elastomer that safely contacts the container 108 and limits the depth to which the container 108 is inserted into the PRP activation system 100.

The portion of the container 108 containing the PRP 104 (i.e., the barrel 134 of the syringe) is formed from a material that minimizes reflection of the shock waves 106, 250 and promotes passage of the shock waves 106, 250 therethrough. For example, in one embodiment, the container 108 is formed from TPX (polymethylpentene (PMP)). The container 108 is typically not formed from glass or polypropylene because these materials tend to reflect rather than transmit shock waves. Whereas, the container 108 formed from TPX minimizes and/or tends to reduce reflection of shock waves because TPX has an acoustic impedance similar to the material of the coupling medium 124 and the PRP 104. Moreover, TPX has a low attenuation to ultrasound. Accordingly, the shock waves 106, 250 pass through the walls of the container 108 and are imparted upon the PRP 104 at the focal volume 258 with minimal reflection and attenuation. In one embodiment, the container 108 includes a 12 ml barrel 134. The PRP activation system 100 is configured to accommodate any size and volume of container 108 provided as vials, test tubes, syringes, and the like.

Figure 4:
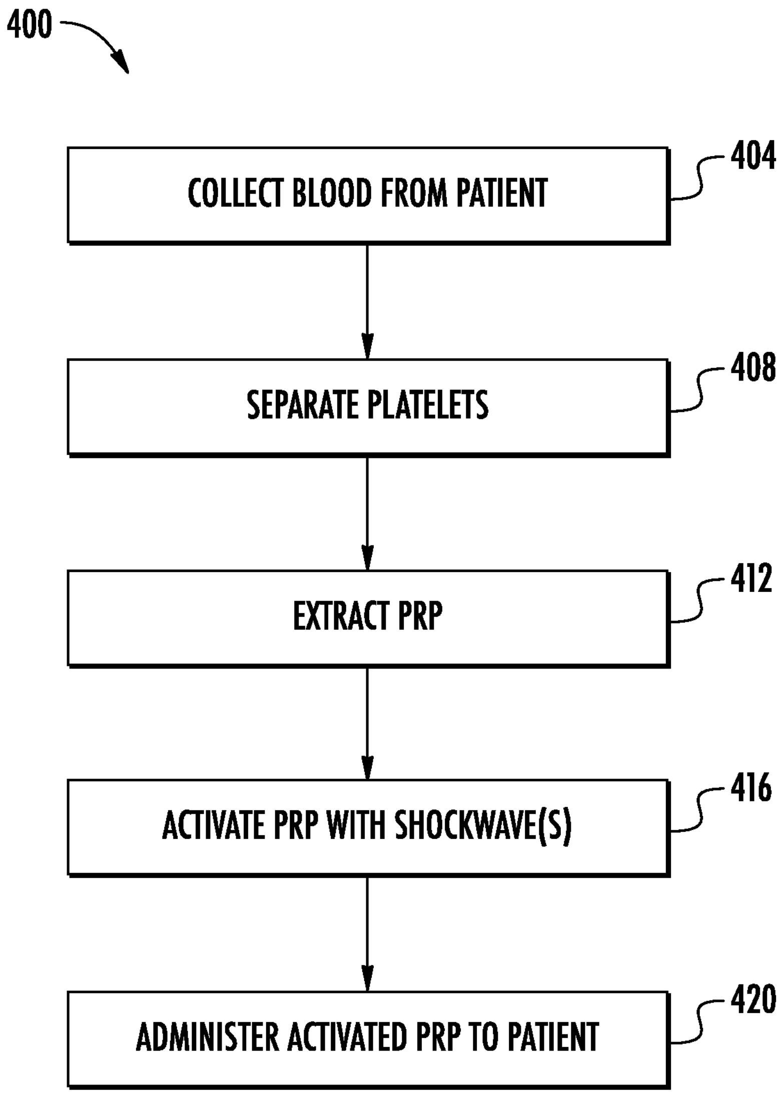
FIG. 4 is a flowchart illustrating an exemplary method of activating PRP using the PRP activation system of FIG. 1.

In operation, the PRP activation system 100 is incorporated in a PRP therapy session. An exemplary usage of the PRP activation system 100 is described by the method 400 illustrated in FIG. 4. The method 400 begins at block 404 by drawing a quantity of blood of a patient. The patient may be a human or animal patient that has suffered a soft tissue injury and/or a joint injury, for example. Exemplary animals that are known to benefit from PRP therapy include horses, dogs, cats, and other mammals. Typically, about 30-60 ml of blood is drawn, but this amount may vary depending on the size and weight of the person or animal.

Next, at block 408 the collected blood is placed in a centrifuge device (not shown) to separate the blood into a red blood cell portion, a PRP portion, and a platelet-poor plasma portion. The centrifuge process typically takes less than fifteen minutes to separate the blood into the above-identified constituents. Any suitable centrifuge device may be used at block 408. Portable centrifuges are available so that the method 400 can be performed at any location.

At block 412, the PRP 104 is extracted from the centrifuged blood. Typically, the PRP 104 is located between the red blood cells (not shown) and the platelet-poor plasma (not shown). The PRP 104 is removed using the container 108 and a corresponding needle (not shown), for example. Any desired process may be used to extract the PRP 104 at block 412 of the method 400. When 30-60 ml of blood is drawn, typically about 3-6 ml of PRP 104 will be extracted therefrom.

Then, at block 416 of the method 400, the extracted PRP 104 is activated using the PRP activation system 100. To activate the PRP 104 using the PRP activation system 100, the container 108 containing the extracted PRP 104 is placed through the opening 284 of the collar 278 and into the housing space 154 of the housing 112. Then, the set screw 280 is gently tightened to secure the position of the container 108 along the movement axis 288.

After container 108 is positioned in the housing 112, the PRP activation system 100 is caused to generate the shock waves 106, 250. The PRP activation system 100 is operated using either the interface 190 or the external device 162. The focused shock waves 106, 250 are generated by the elements 228 and pass through the matching layer 266, the coupling medium 124, and the wall of the container 108. Due to the material of the container 108 (i.e., TPX), the focused shock waves 106 pass through the container 108 and are imparted on and/or strike the PRP 104 at the focal volume 258. When the focused shock waves 106 are imparted on the PRP 104 and/or strike the PRP 104, the PRP 104 is "activated." As used herein, "activating" the PRP 104 causes the PRP 104 to generate and/or to release additional growth factors as compared to unactivated PRP. The growth factors are beneficial to the healing process and improve the efficacy of the PRP therapy.

At block 416, the PRP 104 is activated with a predetermined number of pulses of the focused shock waves 106. For example, the PRP 104 may be activated with from five to one hundred thousand pulses of the focused shock waves 106. In one embodiment, all of the shock wave elements 228 of each shock wave generator assembly 116 are activated during one "pulse" of the focused shock waves 106.

In an exemplary embodiment, the PRP 104 is activated by striking the PRP 104 with approximately 1,000 of the focused shock waves 106 generated at a frequency of 10 Hz and with an energy level of 0.15 $mJ/mm^2$ per focused shock wave 106. In other embodiments, the PRP 104 is activated by striking the PRP 104 with from approximately five to 100,000 of the focused shock waves 106 generated at a frequency of from approximately 1 Hz to 1 kHz, and with an energy level of from approximately 0.05 to 0.50 $mJ/mm^2$ per focused shock wave 106.

In the illustrated embodiment of FIG. 3, the length of the focal volume 258 along the movement axis 288 is approximately the same as the height of the PRP 104 within the container 108. Thus, substantially all of the PRP 104 is struck with the focused shock waves 106 without moving the barrel 134 along the movement axis 288. As used in this context, "substantially" includes at least 90% of the PRP 104.

In other embodiments, the height of the PRP 104 within the container 108 is greater than the length of the focal volume 258 along the movement axis 288. In such a situation, the barrel 134 is moved to a predetermined number of locations or positions during the shock wave activation process of block 416. For example, the container 108 may be moved to three different locations along the movement axis 288 so that three different areas or portions of the PRP 104 are dosed with the focused shock waves 106. The container 108 may be moved from zero to ten different positions along the movement axis 288 during the shock wave process of block 416 depending on the configuration of the container 108 and the amount of the PRP 104 therein. The method 800 of the flowchart of FIG. 8 further describes such a process.

Next, at block 420 the activated PRP 104 is administered to the patient by injecting the activated PRP 104 into the patient at the site of the injury or treatment area. Injecting the activated PRP 104 into the patient typically completes the PRP therapy session.

The shock wave process of activating the PRP 104 at block 416 requires approximately two to five minutes from start to finish. Accordingly, the PRP activation system 100 offers huge advantages over known PRP activation devices and methods. First, there is no cumbersome and expensive refrigeration equipment needed to perform a freeze-thaw cycle to activate the PRP 104. Second, there is no need to wait for the freeze-thaw cycle to conclude. A typical freeze-thaw cycle may take hours or days and significantly delays administration of the activated PRP 104. Third, nothing is added to the unactivated PRP 104, such as calcium chloride ($CaCl_2$) and/or thrombin, which can cause clotting of the activated PRP 104, thereby potentially reducing the effectiveness of the PRP therapy.

Instead, the PRP activation system 100 disclosed herein enables the PRP therapy session to be completed from start (drawing blood, block 404) to finish (injecting the activated PRP 104, block 420) at the side of the patient and within only a few minutes to about 0.5 hour. Moreover, the PRP 104 can be activated anywhere since no connection to an external power source is required. The PRP activation system 100 offers a better quality PRP therapy, in less time, and with nothing added to the patient's blood.

Figure 5A:
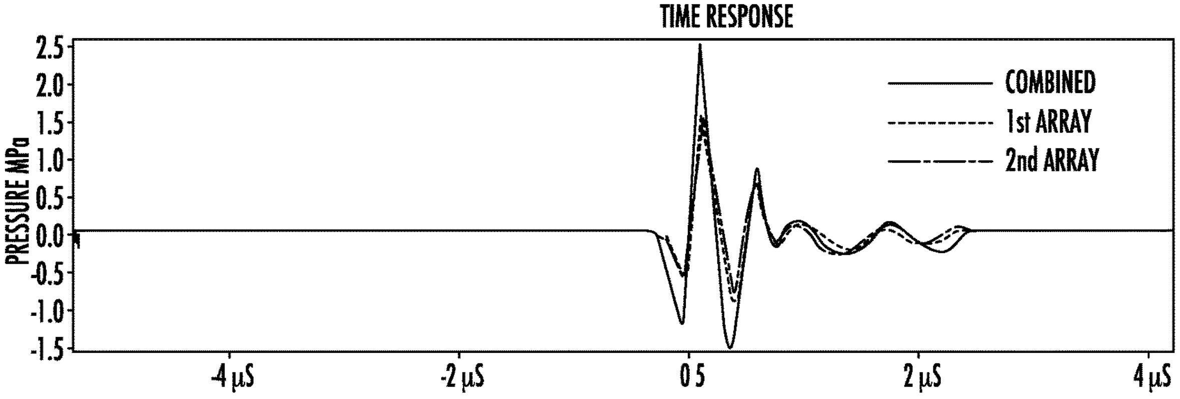
FIG. 5A illustrates a time response test result of the PRP activation system.
Figure 5B:
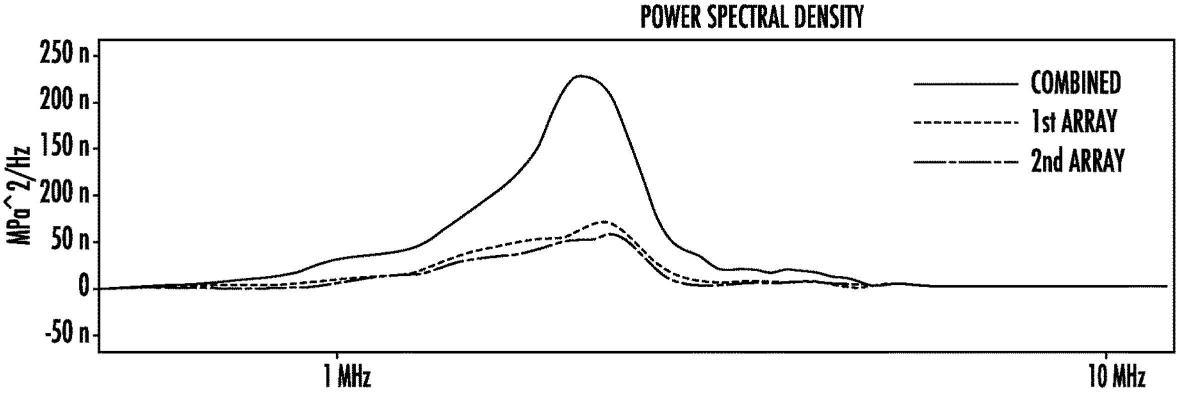
FIG. 5B illustrates a power spectral density test result of the PRP activation system.
Figure 5C:
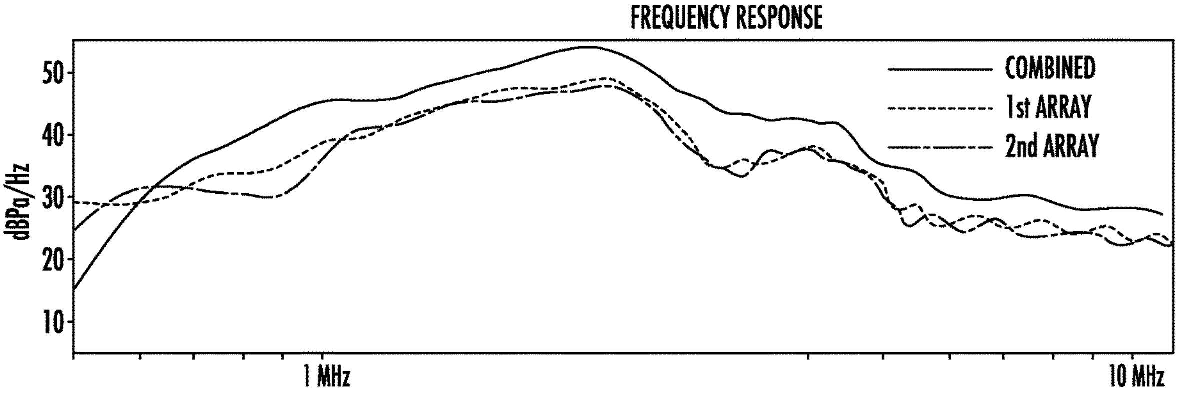
FIG. 5C illustrates a frequency response test result of the PRP activation system.

FIGS. 5A, 5B, and 5C illustrate graphs showing test results of the PRP activation system 100. To conduct the tests, a fiber optic hydrophone probe (Onda HFO-609) is placed in the center of a 10 ml container 108 full of water. In this example, a first focused shock wave 106 from a first array 236 is aimed at the center of the container 108. Then, a second focused shock wave 106 from a different second array 236 is aimed at the center of the container 108 without activating the first array 236. Next, both the first and the second array 236 are activated simultaneously to generate the combined signal shown in the figures. FIG. 5A is a graph of a time response of the focused shock waves 106. As shown in FIG. 5A, the focused shock waves 106 from the first and second arrays 236 are additive and constructively combine to generate the combined signal that has a pressure greater than 2.0 MPa within the container 108 at the focal volume 258. FIG. 5B is a graph of a power spectral density of the focused shock waves 106 and the combined signal. FIG. 5C is a graph of a frequency response of the focused shock waves 106 and the combined signal. Each graph illustrates the additive effect of the focused shock waves 106.

The system used to collect the data shown in the graphs of FIGS. 5A, 5B, and 5C tends to under report high-frequency content in the curves because the propagation direction of the focused shock wave 106 is perpendicular to the axis of the measurement probe, i.e. oblique incidence. Nevertheless, the data shown in the graphs of FIGS. 5A, 5B, and 5C confirms that: 1.) it is possible to transmit shock wave energy from the arrays 236 to the center point 244 of the container 108 at the focal volume 258, and 2.) the energy contributions of multiple arrays 236 (i.e., shock wave generating elements 228) is additive and/or constructively combines. Thus, the data of FIGS. 5A, 5B, and 5C illustrates that the individual shock waves 250 constructively combine to form the focused shock wave 106 that activates the PRP 104 located at the focal volume 258.

Figure 6:
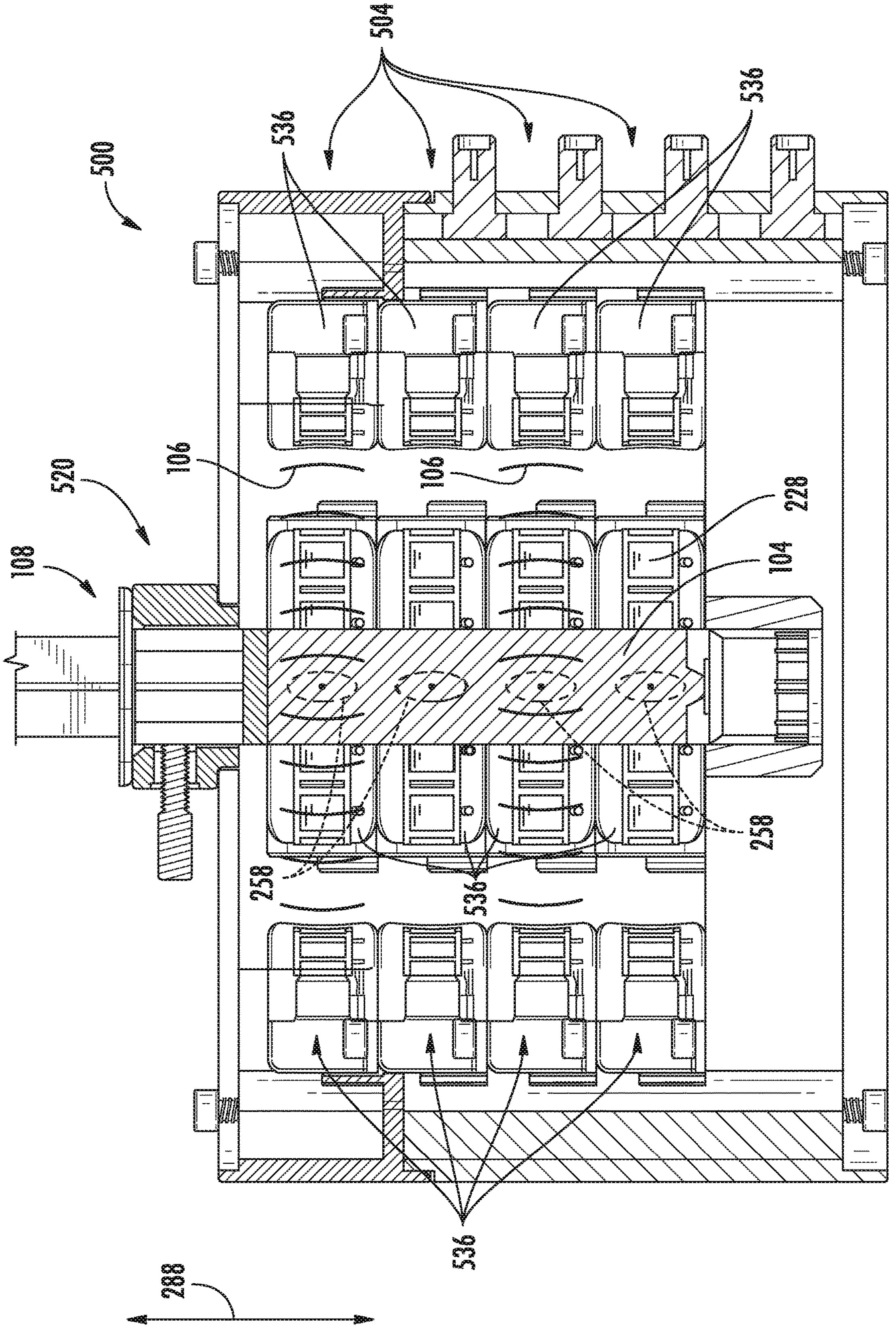
FIG. 6 is a cross sectional view of another embodiment of a PRP activation system, as disclosed herein, including a stacked configuration of concentrically-arranged piezoelectric transducer arrays.

As shown in FIG. 6, another embodiment of a PRP activation system 500 includes a stacked configuration of the transducer arrays 536. In the illustrated embodiment, the PRP activation system 500 includes sixteen of the transducer arrays 536 stacked along the movement axis 288 in four layers 504. The layers 504 are also referred to herein as circumferential belts. Due to the cross sectional view, only twelve of the transducer arrays 536 are shown. Each of the layers 504 includes four of the concentrically-arranged transducer arrays 536. In other embodiments, the PRP activation system 500 includes from two to ten of the layers 504 and may include from two to forty of the transducer arrays 536. Some of the layers 504 may include more or fewer than four transducer arrays 536. For example, some of the layers 504 may include only two of the transducer arrays 536 while other layers 504 of the same PRP activation system 500 may include six, eight, or ten of the transducer arrays 536 depending on the circumferential extent of each of the transducer arrays 536, among other factors. The PRP activation system 500 is otherwise the same as the PRP activation system 500.

The transducer arrays 536 of each layer 504 may be activated to generate the focused shock waves 106 all at once, or the transducer arrays 536 may be activated to generate the focused shock waves 106 one layer 504 at a time. Each layer 504 of activated transducer arrays 536 has a corresponding focal volume 258 within the container 108. That is, the focused shock waves 106 of each layer 504 constructively combine with each other at a corresponding one of the focal volumes 258. The focal volumes 258 are spaced apart from each other along the movement axis 288. The support structure 520 positions the container 108 so that different and spaced apart portions of the PRP 104 are located at each of the focal volumes 558.

The PRP activation system 500 having the multiple focal volumes 558 is configured to activate a greater quantity of the PRP 104 at once than the PRP activation system 100 having only the single focal volume 258. Accordingly, the PRP activation system 500 may prevent the operator from having to move the container 108 to the predetermined number of locations along the movement axis 288 during the shock wave activation process of block 416, because substantially all of the PRP 104 can be activated with the container 108 in a single location.

Figure 7:
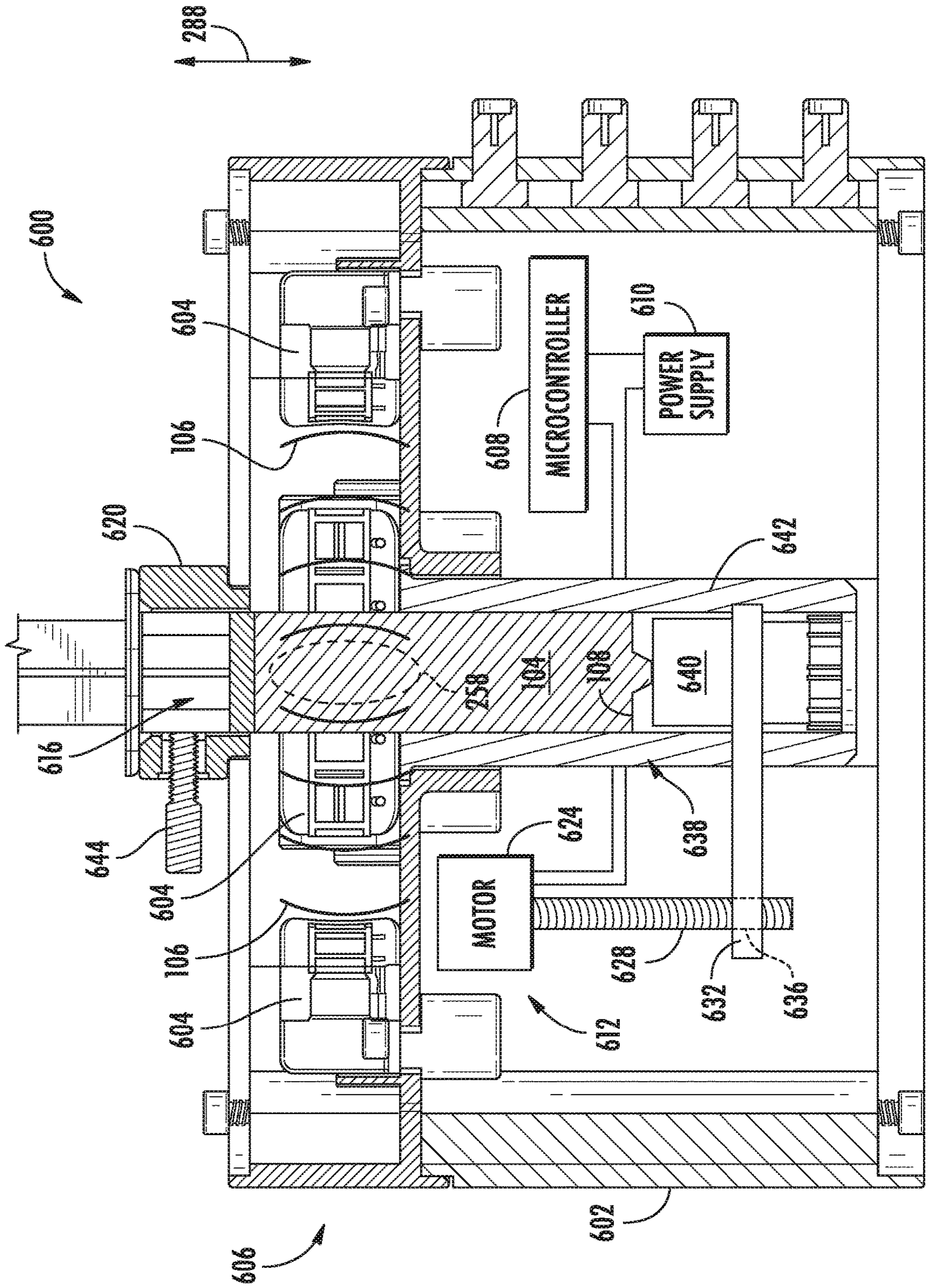
FIG. 7 is a cross sectional view of a further embodiment of a PRP activation system, as disclosed herein, including a positioning device for moving the container along a movement axis, the container is shown in a first position.

As shown in FIG. 7, another embodiment of a PRP activation system 600 includes a housing 602 and four transducer arrays 604 (three are shown in FIG. 7) concentrically arranged in one layer 606, a microcontroller 608, a power supply 610, and a positioning device 612 configured to move the container 108 when the container 108 is positioned in an opening 616 defined by a support structure 620. The PRP activation system 600 is otherwise the same as the PRP activation system 100, and includes corresponding drive electronics, an FPGA, and an interface, which are not shown in FIG. 7.

The microcontroller 608 is the same as the microcontroller 202 and may be provided as any desired processor, microprocessor, controller, and/or microcontroller. In a specific embodiment, the microcontroller 608 is a 32F413 microprocessor by STMicroelectronics.

The positioning device 612, in one embodiment, is operably connected to the microcontroller 608 and the power supply 610, and includes an electric motor 624, a shaft 628, and a lift plate 632. The positioning device 612 is further operably connected to the container 108 for moving the container 108 along the movement axis 288 relative to the support structure 620. In one embodiment, the electric motor 624 is a stepper motor, but in other embodiments the electric motor 624 is any desired type of electric motor including brushed and brushless motor types.

The shaft 628 is a threaded shaft that extends from the electric motor 624 and is rotated by the electric motor 624 either directly or through a gear arrangement (not shown).

The lift plate 632 is operably connected to the shaft 628 and defines an opening 636 configured to threadingly receive the shaft 628. In one embodiment, the lift plate 632 extends through a corresponding slot 638 in the support sleeve 642. Accordingly, the lift plate 632 is prevented from rotating relative to the housing 112, but is movable in both directions along the movement axis 288 in the slot 638. In some embodiments, a spacer block 640 is positioned between the container 108 and the lift plate 632.

In response, to activation of the electric motor 624, the electric motor 624 is configured to rotate the shaft 628. The rotation of the shaft 628 causes the lift plate 632 to move along movement axis 288 to a selected position and/or to a predetermined position. The container 108 rests upon the lift plate 632 and/or the support block 640. Accordingly, the movement of the lift plate 632 moves the container 108 along the movement axis 288. In particular, the movement of the lift plate 632 positions the container 108 so that a predetermined portion of the PRP 104 is in the focal zone 258 of the transducer arrays 604. The predetermined portion of the PRP 104 is struck with the focused shock waves 106.

Figure 8:
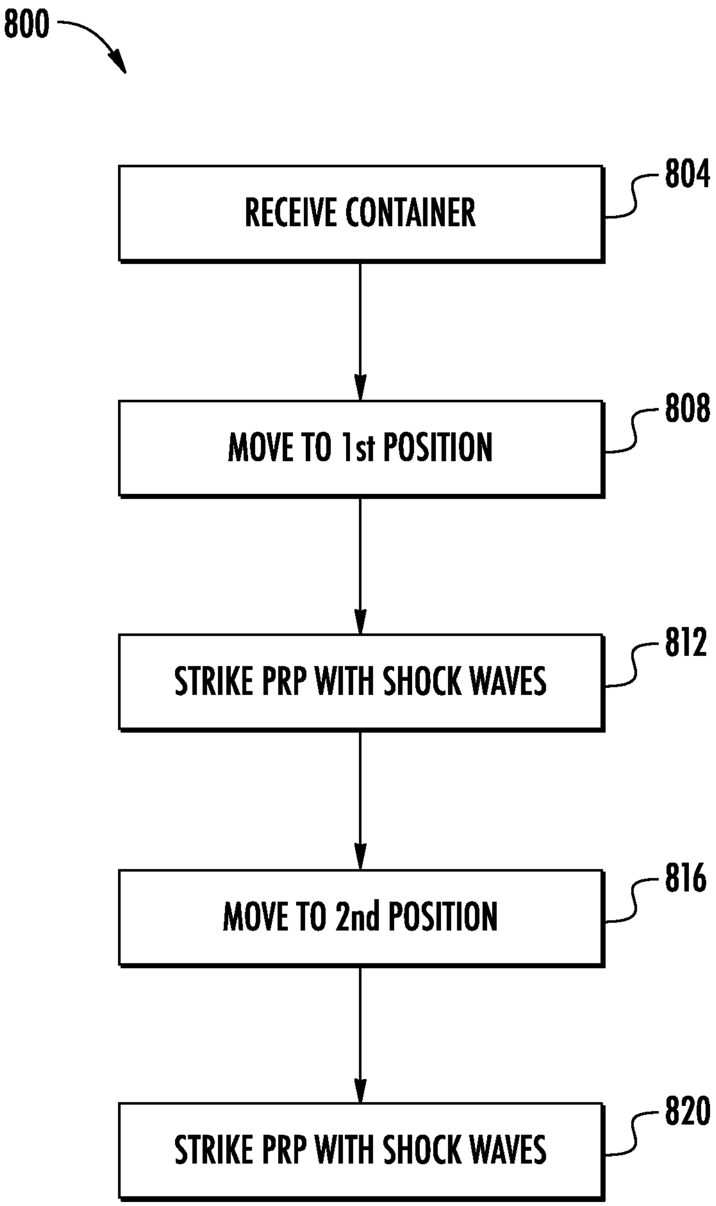
FIG. 8 is a flowchart illustrating an exemplary method of activating PRP using the PRP activation system of FIG. 7.

As shown in FIG. 8, a method 800 of operating the PRP activation system 600 automatically moves the container 108 during activation of the PRP 104 using the positioning device 612. At block 804, the PRP activation system 600 receives the container 108 by placing the container 108 into the opening 616 in the support structure 620. A set screw 644 of the support structure 620 is not tightened so that the container 108 is movable along the movement axis 288 relative to the housing 602 and the support structure 620.

Next at block 808, the microcontroller 608 activates the positioning device 612 to move the lifting plate 632 to the position shown in FIG. 7, which is referred to as a lower position or a first position. At the lower position, the transducer arrays 604 are positioned to strike a first portion of the PRP 104 with the focused shock waves 106.

At block 812 of the method 800, the microcontroller 608 activates the transducer arrays 604 to generate the focused shock waves 106 (i.e., a first focused shock wave), which strike a first portion of the PRP 104 at the focal volume 258. As shown in FIG. 7, there is an additional quantity of the PRP 104 located below the focal volume 258 that is not struck by the focused shock waves 106. Instead of having the user manually move the container 108 along the movement axis 108, and then generate additional focused shock waves 106 to strike the remaining portions of the PRP 104, the PRP activation system 600 is configured to move the container 108 automatically, thereby simplifying this process for the user.

Figure 9:
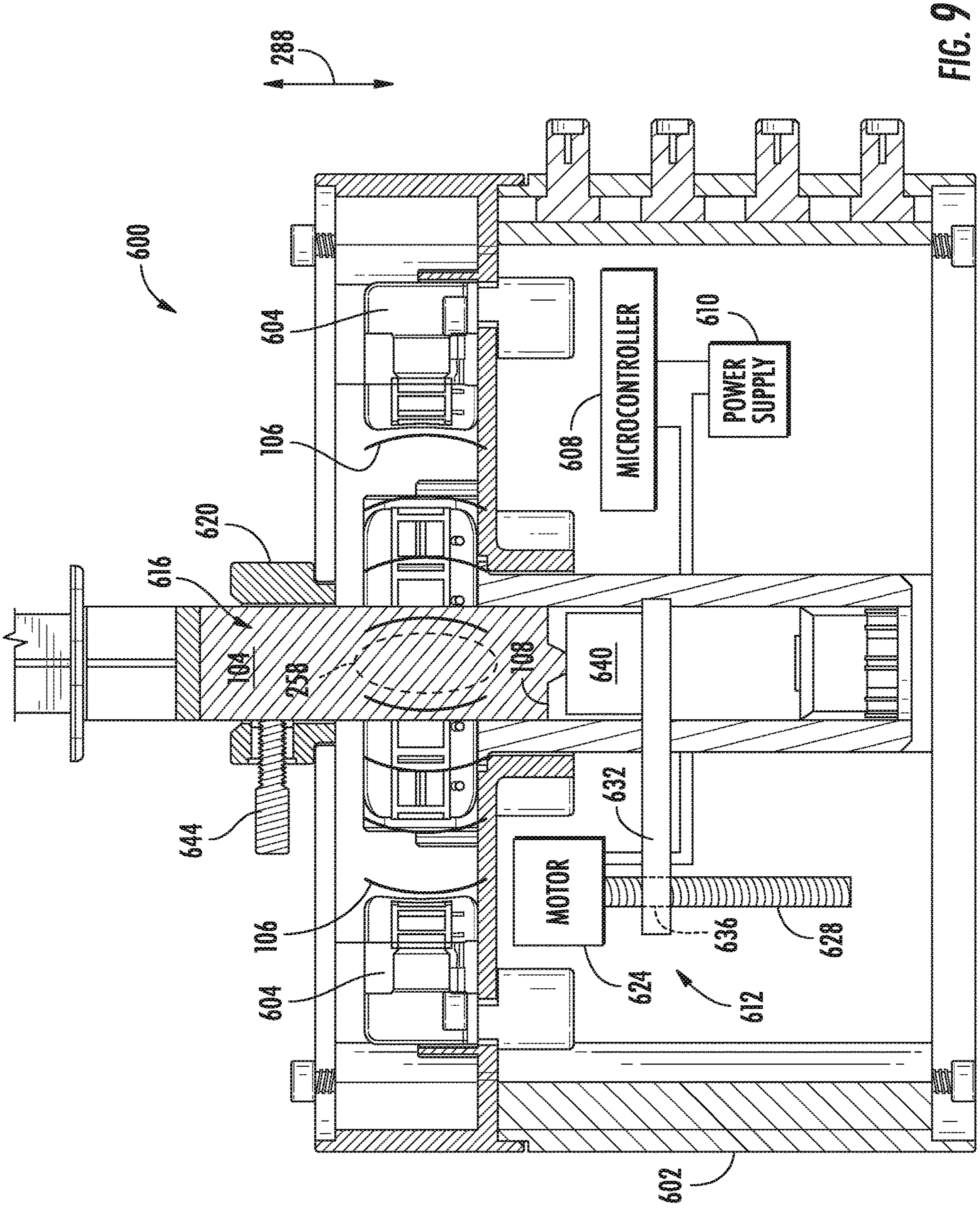
FIG. 9 is another cross sectional view of the PRP activation system of FIG. 7 with the container shown in a second position.

To this end, at block 816 and with reference to FIG. 9, the microcontroller 608 activates the electric motor 624 of the positioning device 612 to move the lift plate 632 to an upper position or a second position along the movement axis 288. In the second position, a different second portion of the PRP 104 is positioned in the focal volume 258 of the transducer arrays 604. The positioning device 612 is configurable to position the container 108 and the PRP 104 so that any desired portion of the PRP 104 is positioned in the focal volume 258.

At block 820, the microcontroller 608 activates the transducer arrays 604 to generate the focused shock waves 106 (i.e., a second focused shock wave), which strike the second portion of the PRP 104 at the focal volume 258. The process of moving the container 108 along the movement axis 288 and striking the PRP 104 is repeated until the entire amount of the PRP 104 is exposed to the focused shock waves. Accordingly, in other embodiments, the positioning device 612 is used to move the container 108 to a third position, which causes a third portion of the PRP 104 to be struck by the focused shock waves 106 at the focal volume 258. The microcontroller 608 and the positioning device 612 automate the positioning and repositioning of the container 108 so that all of the PRP 104 within the container 108 is exposed to the focused shock waves 258 in a fast and convenient manner.

In another embodiment, the positioning device 612 is used to slowly and continuously move the container 108 during generation of the focused shock waves 106. For example, the positioning device 612 is configured to move the container 108 from the lower position to the upper position during a predetermined time period of from thirty seconds to two minutes. During the predetermined time period (i.e., during the continuous movement of the container 108) the transducer arrays 604 generate the focused shock waves 106 at a predetermined frequency ranging from 1 to 100 Hz.

Figure 10:
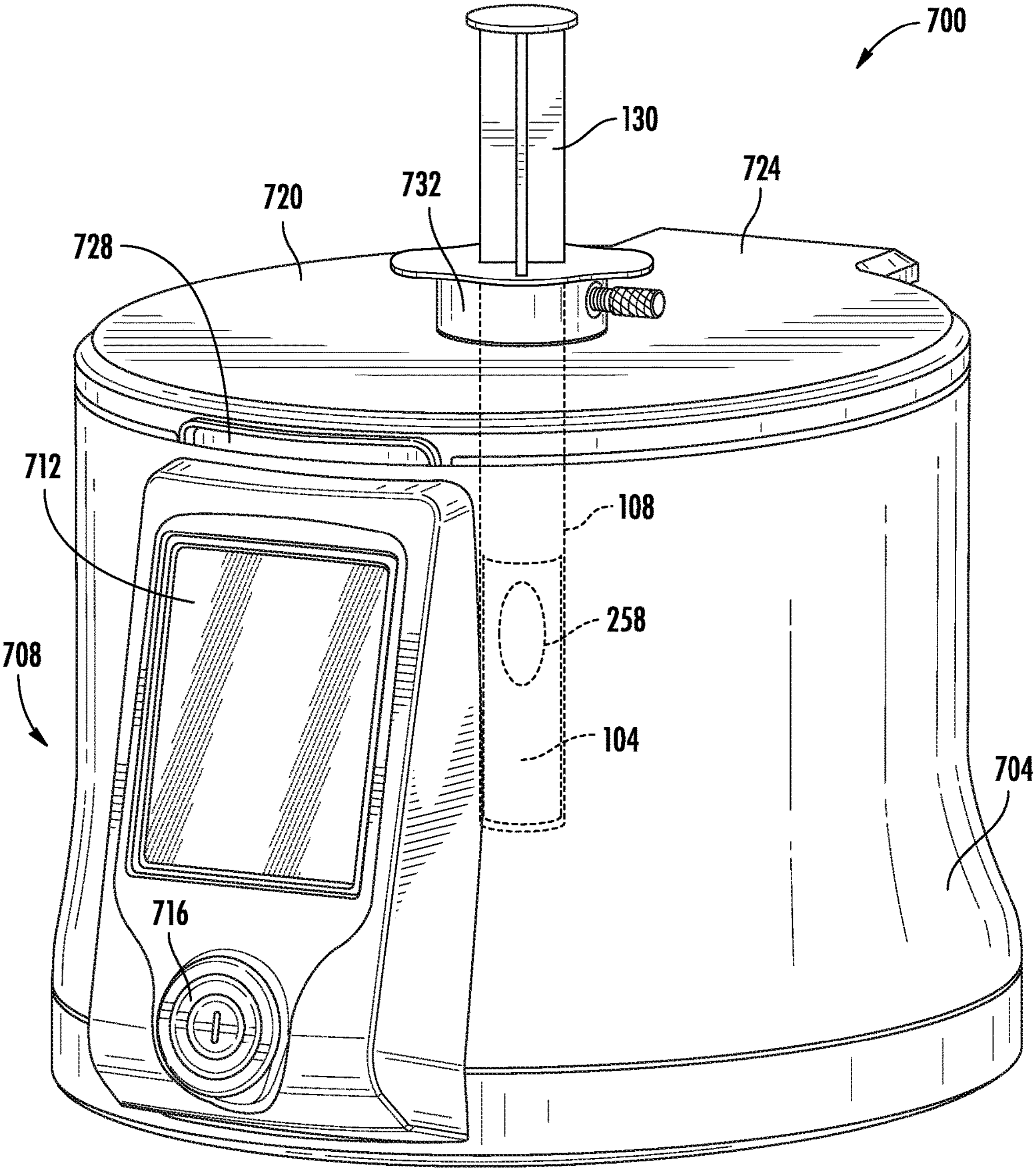
FIG. 10 is a perspective view of yet another embodiment of a PRP activation system, as disclosed herein, including a display and an input device mounted on the housing, the container and the PRP are shown in phantom positioned inside a housing of the PRP activation system.

As shown in FIG. 10, another embodiment of a PRP activation system 700 includes a housing 704 having an interface 708 including a display 712 and an input device 716. The interface 708 is mounted on an exterior of the housing 704.

The display 712 is configured to display information and data pertaining to operation of the PRP activation system 700, such as a number of the focused shock waves 106 (FIG. 2) to be administered to the PRP 104, an energy level of the focused shock waves 106, and a repetition frequency of the focused shock waves 106. In one embodiment, the display 712 is a liquid crystal display (LCD). The display 712 is substantially the same or the same as the display 210.

The input device 716 is configured to generate input data when touched or pressed by the operator. For example, the input device 716 may be pressed to generate an electrical start signal for initiating a shock wave sequence for activating the PRP 104 within the container 108. The input device 716 includes at least one push button. The input device 716 is substantially the same or the same as the input device 214.

A lid 720 of the PRP activation system 700 is operably connected to the housing 704 at a hinge 724. The lid 720 includes a ridge 728 forming a convenient spot for grasping the lid 720 and for opening the lid 720 to access the interior of the housing 704. The lid 720 is opened, for example, to monitor and/or to replace the coupling medium 124 (FIG. 2). With the lid 720 opened, the coupling medium 124 can be removed from the interior of the housing 704 and replaced with a fresh, new, and/or different coupling medium 124.

The PRP activation system 700 is otherwise the same as the PRP activation system 100, and includes corresponding drive electronics, an FPGA, a power supply, and a shock wave generator assembly, which are not shown in FIG. 10. The PRP activation system 700 includes a support structure 732 configured to receive the container 108 and to position the container 108 within the housing 704 so that the PRP 104 is positionable in a corresponding focal volume 258 to receive the focused shock waves 106 generated by the shock wave generator assembly for activating the PRP 104. In some embodiments, the PRP activation system 700 also includes the positioning device 612.

In another embodiment of the PRP activation system 100 the elements 228 are activated simultaneously without the timing sequence that focuses the individual shock waves 250. In this embodiment, the individual shock waves 250 strike the PRP 104 at different times and with a time dispersion that is greater than 20 nanoseconds. Stated differently, the unfocused individual shock waves 250 arrive at the center point 244 over a time period that is greater than 20 nanoseconds. Since, the individual shock waves 250 are not focused, the shock waves 250 strike the PRP 104 with a lower total energy level and with less intensity than the focused shock wave 106, but still with enough energy to activate the PRP 104. In an example, the unfocused shock waves 250 strike the PRP 104 at an energy level that is 50% of the energy level resulting from the focused shock wave 106. As a consequence of the simultaneous activation of the elements 228, the power supply 206 is subject to a greater instantaneous power demand. Thus, the simultaneous activation of the elements 228 tends to use more energy from the power supply 206 and tends to deliver less energy to the PRP 104. Whereas, activating the elements 228 at different times using the timing sequence subjects the power supply 206 to a lower instantaneous power demand, such that activating the elements 228 according to the timing sequence tends to use less energy from the power supply 206 and tends to deliver more energy to PRP 104. Accordingly, the PRP activation system 100 using the timing sequence is well-suited for low energy consumption, high portability, and sufficiently activated PRP 104 using fewer shockwaves 106.

In another embodiment, the PRP activation system 100 includes a different type of shock wave generator assembly 116. For example, instead of a shock wave generator assembly 116 including the piezoelectric elements 228, the shock wave generator assembly 116 includes an electromagnetic shock wave generator (not shown) that is configured to generate the focused shock wave 106 at the focal volume 258. Alternatively, the shock wave generator assembly 116 includes an electro hydraulic transducer (not shown) that is configured to generate the focused shock wave 106 at the focal volume 258.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A platelet-rich plasma (PRP) activation system for activating PRP contained in a container, the PRP activation system comprising:
- a housing;
- a power supply located in the housing;
- a piezoelectric transducer array operably connected to the power supply and located in the housing, the piezoelectric transducer array configured to generate a focused shock wave using power from the power supply;
- a support structure operably connected to the housing and configured (i) to receive the container, and (ii) to position the container at least partially within the housing, such that at least a portion of the PRP is located at a focal volume formed by the focused shock wave; and
- a coupling medium located in the housing and positioned between the piezoelectric transducer array and the container, the coupling medium configured to transmit the focused shock wave from the piezoelectric transducer array to the container.

2. The PRP activation system as claimed in claim 1, wherein:
- the piezoelectric transducer array includes (i) a support frame defining an arc-shaped surface from which a plurality of cavities extend into the support frame, and (ii) a plurality of piezoelectric elements at least partially arranged in the plurality of cavities.

3. The PRP activation system as claimed in claim 2, further comprising:
- a microcontroller configured to activate the plurality of piezoelectric elements according to a timing sequence, such that individual shock waves formed by each corresponding piezoelectric element of the plurality of piezoelectric elements arrive at the focal volume substantially simultaneously as the focused shock wave.

4. The PRP activation system as claimed in claim 3, wherein:
- the timing sequence causes the microcontroller to activate a first piezoelectric element of the plurality of piezoelectric elements at a first time and to activate a second piezoelectric element of the plurality of piezoelectric elements at a second time, and
- the first time is different from the second time.

5. The PRP activation system as claimed in claim 1, wherein the piezoelectric transducer array is a first piezoelectric transducer array and the focused shock wave is a first focused shock wave, the PRP activation system further comprising:
- a second piezoelectric transducer array operably connected to the power supply and located in the housing, the second piezoelectric transducer array configured to generate a second focused shock wave using the power from the power supply,
- wherein the focal volume is a first focal volume, and
- wherein another portion of the PRP is located at a second focal volume formed by the second focused shock wave.

6. The PRP activation system as claimed in claim 1, wherein the piezoelectric transducer array is a first piezoelectric transducer array and the focused shock wave is a first focused shock wave, the PRP activation system further comprising:
- a second piezoelectric transducer array operably connected to the power supply and located in the housing, the second piezoelectric transducer array configured to generate a second focused shock wave using the power from the power supply,
- wherein the focal volume is formed by a constructive combination of the first focused shock wave and the second focused shock wave.

7. The PRP activation system as claimed in claim 6, wherein:
- the first piezoelectric transducer array emits the first focused shock wave in a first direction,
- the second piezoelectric transducer array emits the second focused shock wave in a second direction different from the first direction, and
- the support structure defines an opening configured to receive the container as the container moves in a third direction different from the first direction and the second direction.

8. The PRP activation system as claimed in claim 1, further comprising:
- a positioning device operably connected to the power supply, the positioning device configured to operably connect to the container and to move the container along a movement axis.

9. The PRP activation system as claimed in claim 1, further comprising:
- a matching layer applied to the piezoelectric transducer array,
- wherein the coupling medium is positioned against the matching layer and the container, when the container is at least partially positioned in the housing.

10. The PRP activation system as claimed in claim 1, wherein:
- the power supply is a rechargeable battery that is a power source for generating the focused shock wave, and
- the PRP activation system is connected to no other power source for generating the focused shock wave.

11. A platelet-rich plasma (PRP) activation system for activating PRP contained in a container, the PRP activation system comprising:
- a housing;
- a power supply located in the housing;
- a first piezoelectric transducer array operably connected to the power supply and located in the housing, the first piezoelectric transducer array configured to generate a first focused shock wave using power from the power supply;
- a second piezoelectric transducer array operably connected to the power supply and located in the housing, the second piezoelectric transducer array configured to generate a second focused shock wave using the power from the power supply; and
- a support structure operably connected to the housing and configured (i) to receive the container, and (ii) to position the container at least partially within the housing along a movement axis of the container, such that a first portion of the PRP is located at a first focal volume formed by the first focused shock wave and a second portion of the PRP is located at a second focal volume formed by the second focused shock wave, wherein the first focal volume and the second focal volume are spaced apart from each other along the movement axis.

12. The PRP activation system as claimed in claim 11, further comprising:

a third piezoelectric transducer array operably connected to the power supply and located in the housing, the third piezoelectric transducer array configured to generate a third focused shock wave using the power from the power supply; and a fourth piezoelectric transducer array operably connected to the power supply and located in the housing, the fourth piezoelectric transducer array configured to generate a fourth focused shock wave using the power from the power supply, wherein the third focused shock wave constructively combines with the first focused shock wave at the first focal volume, and wherein the fourth focused shock wave constructively combines with the second focused shock wave at the second focal volume.

13. The PRP activation system as claimed in claim 11, wherein:

the first piezoelectric transducer array includes (i) a first support frame defining a first arc-shaped surface from which a first plurality of cavities extend into the first support frame, and (ii) a first plurality of piezoelectric elements at least partially arranged in the first plurality of cavities, and the second piezoelectric transducer array includes (i) a second support frame defining a second arc-shaped surface from which a second plurality of cavities extend into the second support frame, and (ii) a second plurality of piezoelectric elements at least partially arranged in the second plurality of cavities.

14. The PRP activation system as claimed in claim 13, further comprising:

a microcontroller configured (i) to activate the first plurality of piezoelectric elements according to a first timing sequence, such that individual shock waves formed by each corresponding piezoelectric element of the first plurality of piezoelectric elements arrive at the first focal volume substantially simultaneously as the first focused shock wave, and (ii) to activate the second plurality of piezoelectric element according to a second timing sequence, such that individual shock waves formed by each corresponding piezoelectric element of the second plurality of piezoelectric elements arrive at the second focal volume substantially simultaneously as the second focused shock wave, wherein the first timing sequence is different from the second timing sequence.

15. A method of operating a platelet-rich plasma (PRP) activation system, comprising:

striking a first portion of PRP with a first focused shock wave generated by a first piezoelectric transducer array of the PRP activation system in order to activate the first portion of the PRP, the PRP contained in a container received by the PRP activation system, the container located at a first position;

moving the container along a movement axis from the first position to a second position with a positioning device of the PRP activation system; and striking a second portion of the PRP with a second focused shock wave generated by the first piezoelectric transducer array in order to activate the second portion of the PRP, the container located at the second position.

16. The method as claimed in claim 15, wherein the moving the container along the movement axis includes:

activating an electric motor of the positioning device with a microcontroller of the PRP activation system to move the container along the movement axis.

17. The method as claimed in claim 16, wherein the electric motor is a stepper motor.

18. The method as claimed in claim 15, further comprising:

striking the first portion of the PRP with a third focused shock wave generated by a second piezoelectric transducer array of the PRP activation system, the container located at the first position, wherein the first focused shock wave moves in a first direction, wherein the third focused shock wave moves in a second direction opposite to the first direction, and wherein the first focused shock wave and the third focused shock wave constructively combine at a first focal volume that includes the first portion of the PRP.

19. The method as claimed in claim 18, further comprising:

striking the first portion of the PRP with a fourth focused shock wave generated by a third piezoelectric transducer array of the PRP activation system, the container located at the first position; and striking the first portion of the PRP with a fifth focused shock wave generated by a fourth piezoelectric transducer array of the PRP activation system, the container located at the first position, wherein the fourth focused shock wave moves in a third direction perpendicular to the first direction, wherein the fifth focused shock wave moves in a fourth direction opposite to the third direction, and wherein the first focused shock wave, the third focused shock wave, the fourth focused shock wave, and the fifth focused shock wave constructively combine at the first focal volume.

20. The method as claimed in claim 15, further comprising:

moving the container along the movement axis from the second position to a third position with the positioning device; and striking a third portion of the PRP with a third focused shock wave generated by the first piezoelectric transducer array of the PRP activation system in order to activate the third portion of the PRP, the container located at the third position.

* * * * *